United States Patent
Kamishita et al.

(10) Patent No.: US 11,103,453 B2
(45) Date of Patent: Aug. 31, 2021

(54) RHINOVACCINATION SYSTEM OF INFLUENZA VACCINE

(71) Applicant: TOKO YAKUHIN KOGYO KABUSHIKI KAISHA, Osaka (JP)

(72) Inventors: Taizou Kamishita, Osaka (JP); Takashi Miyazaki, Osaka (JP)

(73) Assignee: TOKO YAKUHIN KOGYO KABUSHIKI KAISHA, Osaka (JP)

( * ) Notice: Subject to any disclaimer, the term of this patent is extended or adjusted under 35 U.S.C. 154(b) by 1103 days.

(21) Appl. No.: 15/322,001

(22) PCT Filed: Jun. 24, 2015

(86) PCT No.: PCT/JP2015/068198
§ 371 (c)(1),
(2) Date: Dec. 23, 2016

(87) PCT Pub. No.: WO2015/199129
PCT Pub. Date: Dec. 30, 2015

(65) Prior Publication Data
US 2017/0128363 A1    May 11, 2017

(30) Foreign Application Priority Data
Jun. 25, 2014 (JP) .............................. JP2014-130365

(51) Int. Cl.
*A61K 9/12* (2006.01)
*A61K 39/145* (2006.01)
*A61K 47/32* (2006.01)
*A61M 11/00* (2006.01)
*C12N 7/00* (2006.01)
*A61K 47/02* (2006.01)
*A61K 39/00* (2006.01)

(52) U.S. Cl.
CPC .............. *A61K 9/12* (2013.01); *A61K 39/145* (2013.01); *A61K 47/02* (2013.01); *A61K 47/32* (2013.01); *A61M 11/00* (2013.01); *A61M 11/001* (2014.02); *A61M 11/007* (2014.02); *C12N 7/00* (2013.01); *A61K 2039/5252* (2013.01); *A61K 2039/543* (2013.01); *A61K 2039/55505* (2013.01); *A61K 2039/55511* (2013.01); *A61M 2206/16* (2013.01); *A61M 2210/0618* (2013.01); *C12N 2760/16034* (2013.01)

(58) Field of Classification Search
None
See application file for complete search history.

(56) References Cited

U.S. PATENT DOCUMENTS

| | | | |
|---|---|---|---|
| 3,669,359 A | 6/1972 | Focht | |
| 5,064,122 A | 11/1991 | Kamishita et al. | |
| 5,215,739 A | 6/1993 | Kamishita | |
| 6,443,370 B1 | 9/2002 | Brulle et al. | |
| 8,347,879 B2 | 1/2013 | Davies et al. | |
| 2009/0275668 A1* | 11/2009 | Kamishita | A61K 9/0043 514/769 |
| 2010/0308082 A1 | 12/2010 | Lamble et al. | |
| 2012/0082697 A1 | 4/2012 | Hasegawa et al. | |
| 2012/0205464 A1 | 8/2012 | Pardonge | |
| 2015/0075520 A1 | 3/2015 | Kakuta et al. | |
| 2016/0015800 A1 | 1/2016 | Hasegawa et al. | |

FOREIGN PATENT DOCUMENTS

| | | |
|---|---|---|
| EP | 0499690 | 8/1992 |
| EP | 0526824 A2 | 2/1993 |
| EP | 1092447 | 4/2001 |
| JP | H02-91553 | 7/1990 |
| JP | H0291553 U | 7/1990 |
| JP | H03-38529 | 2/1991 |
| JP | H03-198866 | 8/1991 |
| JP | H03-114248 | 11/1991 |
| JP | 2002509026 | 3/2002 |
| JP | 2012521965 | 9/2012 |
| JP | 5185109 | 1/2013 |
| JP | 2014091064 | 5/2014 |
| WO | 2007123193 | 11/2007 |
| WO | 2010114169 | 10/2010 |
| WO | 2013145789 | 10/2013 |
| WO | 2014103488 A1 | 7/2014 |

OTHER PUBLICATIONS

International Search Report of International Application No. PCT/JP2015/068198, dated Sep. 15, 2015, total 2 pages.
International Search Report of International Application No. PCT/JP2015/068199, dated Sep. 8, 2015, total 3 pages.
Chinese Office Action issued in Chinese Application No. 201580033814.8, dated Aug. 23, 2019, 12 pages including English translation.
Oka et al., "Influenza vaccine: enhancement of immune response by application of carboxy-vinylpolymer", Vaccine, vol. 8, Dec. 1990, p. 573-576, 4 pages.
Ainai et al., "Intranasal vaccination with an inactivated whole influenza virus vaccine induces strong antibody responses in serum and nasal mucus of healthy adults", Human Vaccines & Immunotherapeutics, vol. 9, Issue 9, p. 1962-1970; Sep. 2013, 10 pages.
The extended European Search Report issued in European Patent Application No. 15811504.8 dated Dec. 19, 2017, 8 pages.

(Continued)

*Primary Examiner* — Benjamin P Blumel

(74) *Attorney, Agent, or Firm* — Hamre, Schumann, Mueller & Larson, P.C.

(57) ABSTRACT

The present invention relates to a rhinovaccination system of influenza vaccine, comprising a medical syringe filled with an influenza vaccine composition which comprises an inactivated whole influenza virion and a gel base material comprising carboxy vinyl polymer to administer the influenza vaccine composition to nasal mucosa, which is characterized by not comprising an adjuvant.

10 Claims, 7 Drawing Sheets

(56) References Cited

OTHER PUBLICATIONS

International Preliminary Report on Patentability of International Application No. PCT/JP2015/068198, dated Dec. 27, 2016, total 8 pages.
International Preliminary Report on Patentability of International Application No. PCT/JP2015/068199, dated Dec. 27, 2016, total 12 pages.
The extended European search report issued in EP15811100.5 dated Feb. 6, 2018, 7 pages.
Birkhoff, M. et al., "Advantages of Intranasal Vaccination and Considerations on Device Selection", Indian Journal of Pharmaceutical Sciences, 2009, p. 729-731.
Office Action issued for Indian Patent Application No. 201747002050, dated Apr. 7, 2021, 7 pages.

\* cited by examiner (a)

(b)

RHINOVACCINATION SYSTEM OF INFLUENZA VACCINE

TECHNICAL FIELD

The present invention relates to a rhinovaccination system to administer an influenza vaccine composition to nasal mucosa, which is used in combination with a medical syringe.

BACKGROUND ART

Influenza is an acute respiratory tract infection caused by the influenza virus, in particular, influenza becomes epidemic in winter year after year. In addition, influenza sometimes results in a pandemic, and many people become severe to result in death. For influenza, it is known that the vaccination with influenza vaccine can bring in some preventive effects, thus people are broadly vaccinated before the epidemic season.

The influenza vaccine approved in Japan is only an inactivated protein-component of an influenza viral antigen to be subcutaneously vaccinated, and currently, a split vaccine thereof is used as the seasonal influenza vaccine. Such vaccine to be subcutaneously vaccinated is highly effective for preventing the severity in influenza infection such as pneumonia, but it has low antibody-induced activity in upper respiratory mucous membrane that is an infected area of influenza virus, which is not enough as infective protection-activity. And, such injection administration has problems, for example, a pain and side-effects such as inflammation caused by topical vaccination.

For the above problem of influenza vaccination, a wide variety of the trials have been done until now, in which a vaccine for nasal administration has received attention as a new vaccination. However, it has been reported that it is impossible to induce a high immune response to the influenza virus even though the split vaccine which has been broadly used in current clinical practice is nasally administered to experimental animals or human beings directly.

Under such circumstances, the world's first split influenza vaccine for nasal administration which comprises *Escherichia coli* heat labile toxin as an adjuvant was approved in Switzerland [Berna Biotech, Switzerland; Commercial name: Nasalflu], and the sale thereof started in October, 2000, but the clinical use thereof was withdrawn in February, 2004 due to the toxicity of the adjuvant. And, Patent Reference 1 also discloses an influenza vaccine for nasal administration which comprises an adjuvant, which indicates that the immune induction can be enhanced by using the adjuvant. However, the toxicity of adjuvants is an anxious matter for practical use.

For the nasal administration, it is also necessary to consider the complicated structure of nasal cavity, and it is desirable to make influenza vaccine broadly spread, attached and retained for a long time in nasal cavity. For example, the base (material) disclosed in Patent Reference 2 may be used for spray-administration.

The pump-type spray device such as an airless-type spray device used in Patent Reference 2 can achieve a good spray-suitability of a formulation (spray-dispersibility, uniformity of formulation particle size, etc.), which is expected to gain the desired enough drug efficacy, however, it is difficult to fill the spray container with only one dose to make it one-shot administration system, from the point of the structure of the spray container. Thus, in order to nasally administer an influenza vaccine with such pump-type spray device, there was no other way but to fill the spray container with a large excess vaccine formulation, administer it to one person, and then dispose of the rest with the spray device or share the rest with plural subjects from the viewpoint of the cost. However, the repetitive use of such airless-type spray device's tip in nasal cavity of plural patients or subjects can make most of people feel emotionally bad, and the use is unsanitary and in danger of another infection (hospital infection).

As mentioned above, it has been desired to develop influenza vaccine for nasal administration as a next-generation influenza vaccine and put it to practical use, which takes the place of a conventional influenza vaccine for subcutaneous or intramuscular administration. However, there are various problems for the practical use, for example, how the toxicity of an adjuvant used to enhance the immune induction should be reduced, or how the device for administration should be devised to enhance its effect enough.

PRIOR ART

[Patent Reference 1] WO 2010/114169
[Patent Reference 2] WO 2007/123193

SUMMARY OF INVENTION

One of the purposes of the present invention is to provide a system to administer an influenza vaccine composition for spray-administration to nasal mucosa which is prepared by using an inactivated whole influenza virion as an antigen that has been already approved, but not using an adjuvant, which exhibits a high efficacy and low side effects in spite of a low antigen level, which is used in combination with a device for administration.

In addition, WO 2014/103488 is an application related to the present application, which has already been published. However, the priority date of the present application is earlier than the published date of the related application, and thus it is not a prior art document for the present application.

The present inventors have extensively studied on the above problem and then have found that a combination of (i) a gel base (material) for spray-administration to nasal mucosa comprising carboxy vinyl polymer which is treated by adding an outside shearing force to add spray-performance and (ii) an inactivated whole influenza virion, can enhance the immune induction in human beings without an adjuvant; and further have made an administration system by setting the combination into a metered-dose syringe-based squirt having an optimized shape/configuration of the nozzle. Based upon the new findings, the present invention has been accomplished. The present invention may provide the following embodiments.

[1] A rhinovaccination system of influenza vaccine, comprising a syringe-based squirt filled with an influenza vaccine composition which comprises (i) an inactivated whole influenza virion, and (ii) a gel base material comprising carboxy vinyl polymer which is treated by adding an outside shearing force to add spray-performance, which is characterized by not comprising an adjuvant.

[2] The rhinovaccination system of influenza vaccine according to [1], wherein the syringe-based squirt is a medical syringe having a tip opening in fluid communication with a syringe barrel, which is equipped with a rhinal spray nozzle comprising a hollow nozzle body having a tip portion defining a nozzle orifice thereon, a solid packing rod arranged within the nozzle body, and a nozzle chamber defined between the packing rod and the nozzle body to allow a fluid communication between the tip opening and the nozzle orifice, wherein the nozzle orifice has a diameter in a range between 0.25 mm and 0.30 mm.

[3] The rhinovaccination system of influenza vaccine according to [1] or [2], wherein the amount of (i) the inactivated whole influenza virion is 1-500 μg HA/mL per type of vaccine virus strain.

[4] The rhinovaccination system of influenza vaccine according to any one of [1] to [3], wherein the influenza vaccine composition comprises 0.1 w/v % to 1.0 w/v carboxy vinyl polymer.

[5] The rhinovaccination system of influenza vaccine according to any one of [1] to [4], wherein the spray-performance is to control (1) the particle-size-distribution of the sprayed composition, (2) the uniformity of spray density, and/or (3) the spray angle.

[6] The rhinovaccination system of influenza vaccine according to any one of [1] to [3], wherein the influenza vaccine composition is prepared by treating a gel base material comprising 0.5 w/v % to 2.0 w/v % carboxy vinyl polymer by adding an outside shearing force to control (1) the particle-size-distribution of the sprayed composition, (2) the uniformity of spray density, and/or (3) the spray angle, as spray-performance, to give a gel base material, and then mixing the resulting gel base material with a virus stock solution comprising an inactivated whole influenza virion homogeneously in a short time without stress.

[7] The rhinovaccination system of influenza vaccine according to any one of [1] to [6], wherein the influenza vaccine composition is prepared with a gel base material comprising carboxy vinyl polymer that is treated by adding an outside shearing force to add spray-performance which is to control that (1) as for the particle-size-distribution of the sprayed composition, the mean particle size is in a range of 30 μm to 80 μm, and the particle distribution between 10 μm and 100 μm is 80% or more, (2) the spray density is uniform to form a homogeneous full-corn shape, and (3) the spray angle is adjusted in a range of 30° to 70°.

[8] The rhinovaccination system of influenza vaccine according to any one of [1] to [6], wherein the influenza vaccine composition is prepared with a gel base material comprising carboxy vinyl polymer that is treated by adding an outside shearing force to add spray-performance which is to control that (1) as for the particle-size-distribution of the sprayed composition, the mean particle size is in a range of 40 μm to 70 μm, and the particle distribution between 10 μm and 100 μm is 90% or more, (2) the spray density is uniform to form a homogeneous full-corn shape, and (3) the spray angle is adjusted in a range of 40° to 60°.

[9] The rhinovaccination system of influenza vaccine according to any one of [2] to [8], wherein the nozzle orifice includes substantially no curved portion.

[10] The rhinovaccination system of influenza vaccine according to any one of [2] to [9], wherein the tip portion defining the nozzle orifice has thickness along an injection direction of the formulation which is in a range between 0.20 mm and 0.30 mm.

[11] The rhinovaccination system of influenza vaccine according to any one of [2] to [10], wherein the nozzle body includes an inner wall having at least a portion formed in a cylindrical shape and the packing rod includes an outer wall at least a portion formed in a cylindrical shape having a plurality of circumferentially spaced grooves, wherein the nozzle chamber is defined between the at least portion of the inner wall of the nozzle body and the at least portion of the outer wall of the packing rod, and wherein the packing rod includes a vortex-flow generation member opposed to the tip portion of the nozzle body.

[12] The rhinovaccination system of influenza vaccine according to [11], wherein the vortex-flow generation member is formed so that a flow direction of the formulation from the grooves of the packing rod is offset to a central axis, thereby to generate a vortex flow of the formulation.

[13] The rhinovaccination system of influenza vaccine according to [11] or [12], wherein the at least portion of the inner wall of the nozzle body is formed to have a cross section substantially-perpendicular to the injection direction which is continuously or step-wisely reduced towards the injection direction.

The present invention have made it possible to provide an influenza vaccine composition comprising an inactivated whole influenza virion as an active ingredient, but not comprising an adjuvant, which induces a high immune response in spite of a small antigen level, and low side effects because the composition does not comprise an adjuvant. By using an administration system equipped with a metered-dose syringe-based squirt having an optimized-shaped rhinal spray nozzle, the influenza vaccine composition is expected to be suitably applied for the epidemic of influenza.

The influenza vaccine composition of the present invention can be broadly spread, attached and retained for a long time in nasal mucosa because the composition comprises a gel base material comprising carboxy vinyl polymer which is treated by adding an outside shearing force to add spray-performance, thus the influenza vaccine composition of the present invention can induce a high immune response in spite of a small antigen level.

According to the process for preparing an influenza vaccine composition of the present invention, an influenza vaccine composition can be provided, which well keeps the antigenicity of the inactivated whole virion because the virion is treated in a short time without stress, and induces a high immune response and low side effects.

Although the present invention comprises no adjuvant as an immunopotentiating agent, the present invention can provide an equal or more potent immune-induction for upper respiratory mucous membrane and whole body, compared with a composition comprising influenza virus vaccine and an adjuvant.

DESCRIPTION OF EMBODIMENTS

Figure 1:
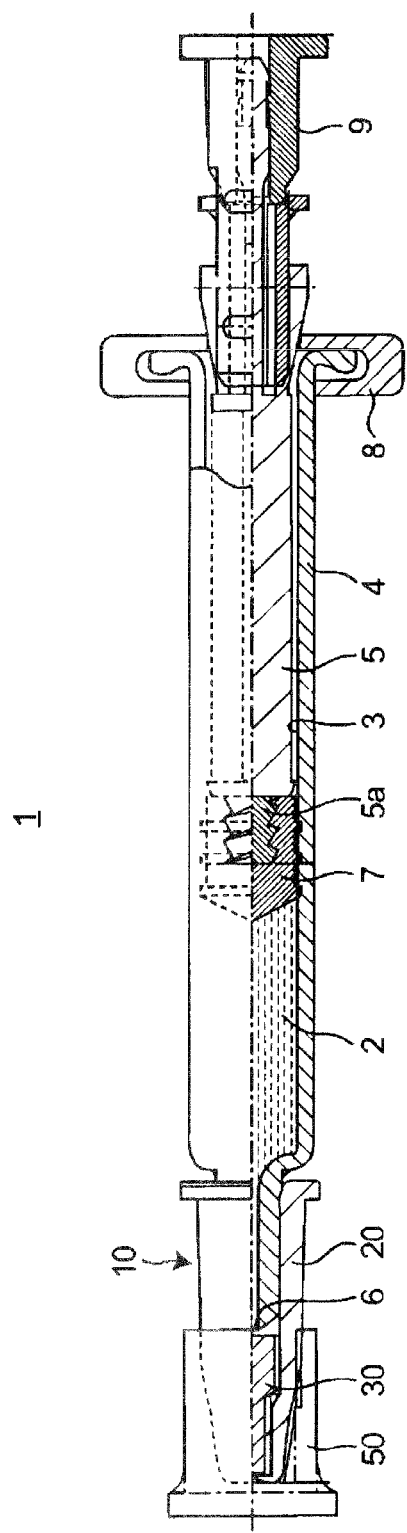
FIG. 1 is a partially-fragmented side view of a general structure of a medical syringe comprising a rhinal spray nozzle of one embodiment according to the present invention.

The present invention provides a rhinovaccination system of influenza vaccine, comprising a medical syringe having a tip opening in fluid communication with a syringe barrel, which is equipped with a rhinal spray nozzle comprising a hollow nozzle body having a tip portion defining a nozzle orifice thereon, a solid packing rod arranged within the nozzle body, and a nozzle chamber defined between the packing rod and the nozzle body to allow a fluid communication between the tip opening and the nozzle orifice, wherein the nozzle orifice has a diameter in a range between 0.25 mm and 0.30 mm, which is filled with an influenza vaccine composition which comprises a gel base material comprising carboxy vinyl polymer which is treated by adding an outside shearing force to add spray-performance, and an inactivated whole influenza virion, which is characterized by not comprising an adjuvant.

The "gel base material comprising carboxy vinyl polymer which is treated by adding an outside shearing force to add spray-performance" used herein means, for example, a "gel base material comprising a skin/mucosa-adhesive agent" disclosed in WO 2007/123193, which is a base material comprising carboxy vinyl polymer and optionally comprising gellan gum, whose viscosity is adjusted by adding an outside shearing force. The base material is characterized in that the viscosity thereof can be adjusted to various ones by adding an outside shearing force, and the spray spreading-angle from a spray container and the spray density can be controlled to meet the purpose. In addition, the use of the present administration system equipped with a metered-dose syringe-based squirt having an optimized-shaped rhinal spray nozzle can achieve a good spray-suitability of a formulation (spray-dispersibility, uniformity of formulation particle size, etc.), as is the case with the pump-type spray device such as an airless-type spray device disclosed in WO 2007/123193, and thereby the use can make the spreading of an inactivated whole influenza virion in nasal mucosa in a wide spread and in a long time to enhance the immunogenicity of an antigen.

Carboxy vinyl polymer which is a material ingredient of the gel base material in the present invention is a hydrophilic polymer prepared by polymerizing acrylic acid as a main ingredient, which can be chosen from pharmaceutical additives that are generally used to prepare an aqueous gel agent without any limitation.

The content of the gel base material comprising carboxy vinyl polymer which is treated by adding an outside shearing force to add spray-performance is 0.1-1.0 w/v %, preferably 0.3-0.7 w/v % as the content of carboxy vinyl polymer.

The vaccine of the present invention is characterized by comprising an inactivated whole influenza virion as an antigen. The inactivated whole influenza virion used herein means a virion which is prepared by cultivating influenza virus to give a virus suspension thereof and purifying the virus suspension while keeping its virus morphology. Thus, the influenza vaccine of the present invention means a vaccine except split vaccine (including subvirion) and subunit vaccine (including purified HA or NA), and it is also referred to as whole virus vaccine.

The above-mentioned inactivated whole influenza virion is preferably such virion that is purified from a virus suspension in the absence of surfactants and ethers. The virus stock solution used herein means a virus solution comprising an inactivated whole influenza virion, which is purified or concentrated to be mixed with a gel base material in the present invention. With regard to the vaccine of the present invention, the concentration of an inactivated whole influenza virion is preferably 1-500 μg HA/mL (in HA equivalent), more preferably 20-250 μg HA/mL (in HA equivalent) per type of vaccine virus strain. The above-mentioned concentration can be determined by measuring the concentration of HA protein.

The influenza virus used herein includes all types of currently-known influenza virus and all subtypes thereof, as well as all types and all subtypes of influenza virus isolated or identified in future. In addition, from the viewpoint of the necessity to also effectively prevent an infection that has not become epidemic in human beings until now, but might become epidemic in human beings in future, a combination of an influenza A virus subtype selected from the group consisting of subtypes H1-H16 excluding subtype H1 and H3 (i.e., H2, and H4-H16) and an influenza A virus subtype selected from the group consisting of subtypes N1-N9 is preferable. These subtypes are also referred to as a new type influenza virus. As the above-mentioned subtypes, a combination of a subtype selected from the group consisting of subtypes H5, H7, and H9 and a subtype selected from the group consisting of subtypes N1-N9 is more preferable. The influenza virus may be derived from a type of strain, two or more types of strains belonging to the same subtype, or two or more types of strains belonging to different subtypes.

The influenza virus used herein includes a strain isolated from infected animals or humans, and a recombinant virus genetically-established at cultured cells. As the method for cultivating influenza virus, the virus may be seeded in the allantoic cavity of eggs of hen and cultivated, or may be infected in cultured cells and cultivated.

An adjuvant is a generic term of substances having the modulating-activity of the immune response such as enhancement and suppression, and is used as an immunopotentiating agent to be added to a vaccine to enhance the immunogenicity of an antigen. Until now, a lot of adjuvants have been studied. The use of an adjuvant enhances the immune effect of a vaccine, but it has disadvantages of side effects such as inflammation. Some adjuvants can be chosen as a candidate to be used in a vaccine for nasal administration, but there has not been any approved vaccine for nasal administration comprising an adjuvant because there has been no adjuvant having a pervasive safety.

The present inventors have found that it is possible to prepare a vaccine having a high efficacy and low side effects in spite of non-adjuvant and a lower antigen level when the gel base material which has the above-mentioned useful spray-performance such as high adhesive property to nasal mucosa is used with the above-mentioned whole-virus vaccine. In addition, the present inventors have also found that using a device which can spray even a gel base material having high viscosity, an influenza vaccine composition can be sprayed to nasal mucosa, wherein the mean particle size of the sprayed composition is in a suitable range of 30 µm to 80 µm (preferably a range of 40 µm to 70 µm), the particle-size-distribution between 10 µm and 100 µm is 80% or more (preferably, 90% or more), the spray angle from the device is set at a range of 30° to 70° (preferably, a range of 40° to 60°) so that the composition can be administered to the desired site in nasal cavity, and the spray density is uniform form a homogeneous full-corn shape. Further the present inventors have also found its process and a method for preventing influenza using the composition. Based upon the new findings, the present invention has been accomplished.

The vaccine of the present invention can comprise an additional pharmaceutically-acceptable carrier(s) besides an inactivated whole influenza virion and a gel base material. The carrier used herein can be a carrier which is generally used in the preparation of a vaccine or a formulation for administration in nasal cavity, which includes, for example, saline, buffered saline, dextrose, water, glycerin, isotonic aqueous buffer solution, and a combination thereof. And, the vaccine of the present invention may optionally include a preservative (e.g. thimerosal), an isotonic agent, a pH regulator, a surfactant, and an inactivating agent (e.g. formalin).

The vaccine of the present invention is used for spray-administration into the nasal cavity.

The vaccine of the present invention can prevent influenza or relieve the symptom thereof.

For the administration of the vaccine, the spray is done to one or both nares with an optimized nose-spray nozzle of the present invention, which can be used as a disposable device.

The dosage of the vaccine should be decided considering the age, sex and weight of a patient or other factors, and actually the vaccine can be administered in an amount of generally 1 µg HA-150 µg HA, preferably 5 µg HA-50 µg HA as an antigen per type of vaccine virus strain.

With reference to attached drawings, embodiments of a rhinal spray nozzle used for a metered-dose syringe-based squirt having the rhinal spray nozzle according to the present invention will be described hereinafter. In the following description, directional terms such as "front, "rear", "proximal" and "distal" are conveniently used for better understandings, however, those terms are not intended to limit the scope of the present invention. Also, like components are denoted by like reference signs throughout the attached drawings.

(Medical Syringe)

FIG. 1 is a partially-fragmented side view of medical syringe 1 comprising rhinal spray nozzle 10 of an embodiment according to the present invention. As illustrated in FIG. 1, medical syringe 1 generally comprises syringe body 4 made of synthetic resin or glass having syringe barrel 3 capable of storing a pharmaceutical formulation therein, and plunger rod 5 inserted within syringe barrel 3 of syringe body 4. Medical syringe 1 also comprises piston 7 having fixing member 5a provided at the distal end of plunger rod 5 and sliding within syringe barrel 3 so as to pump the formulation in syringe barrel 3 out of distal tip opening 6 of syringe body 4, finger flange 8 provided around a proximal end of syringe body 4, and plunger end member 9 transmitting the force applied by a practitioner such as a medical doctor to plunger rod 5. Medical syringe 1 may be similar to the metered-dose syringe-based squirt disclosed in WO 2013/145789.

It should be noted that rhinal spray nozzle 10 of the present invention may be applicable to any type of medical syringes 1 which pump the formulation in syringe barrel 3 by pushing plunger rod 5 (and piston 7), and thus, the present invention will not be limited to the known configurations of the medical syringe. Therefore, the present disclosure will eliminate further description for the detailed structure of medical syringe (or metered-dose syringe-based squirt) 1, and discuss in more detail about the structure and the function of rhinal spray nozzle 10 used for the medical syringe. It should be noted that the disclosure of WO 2013/145789 is incorporated herein by reference into the present application.

(Rhinal Spray Nozzle)

Figure 2:
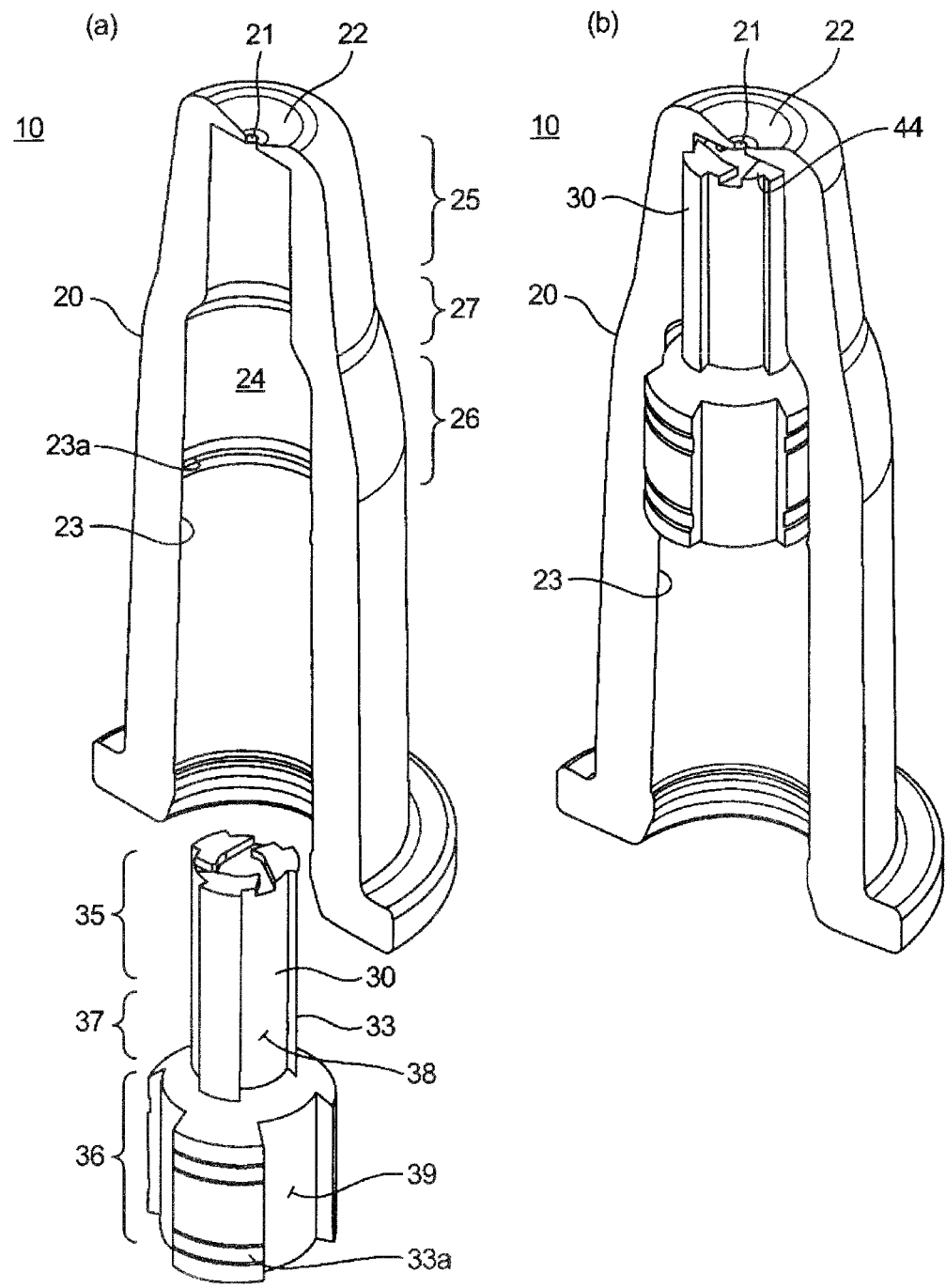
FIGS. 2(a) and 2(b) are partially-fragmented perspective views of the general structure of the rhinal spray nozzle of one embodiment of the present invention, showing configurations before and after the packing rod are inserted within the nozzle body, respectively.

As shown in FIG. 1, medical syringes 1 further comprises rhinal spray nozzle 10 opposed to tip opening 6 of syringe body 4, and protection cap 50 for protecting sterilized tip portion 22 of rhinal spray nozzle 10 from contaminant and mechanical impact. FIGS. 2(a) and 2(b) are partially-fragmented perspective views, showing the general structure of rhinal spray nozzle 10 of an embodiment of the present invention. As shown, rhinal spray nozzle 10 generally comprises hollow nozzle body 20 having tip portion 22 with nozzle orifice 21 and solid packing rod (packing bar) 30 provided within nozzle body 20. FIGS. 2(a) and 2(b) show rhinal spray nozzle 10 before and after packing rod 30 is arranged or inserted within nozzle body 20, respectively. Tip portion 22 of nozzle body 20 has a circular shape and is provided with nozzle orifice 21 at the center thereof.

Figure 3:
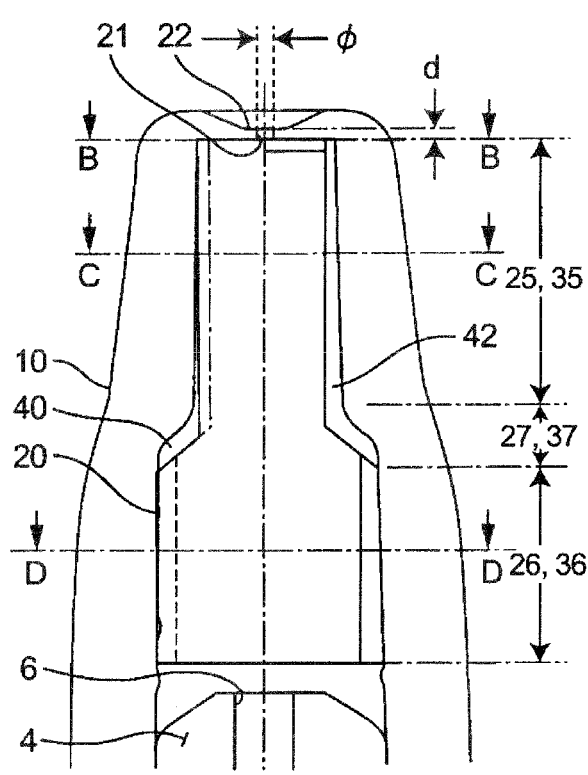
FIG. 3(a) is a vertical cross-sectional view of the rhinal spray nozzle of FIG. 2(b), and FIGS. 3(b), 3(c) and 3(d) are horizontal cross-sectional views of the rhinal spray nozzle taken along B-B line, C-C line and D-D line of FIG. 3(a), respectively.
Figure 3:
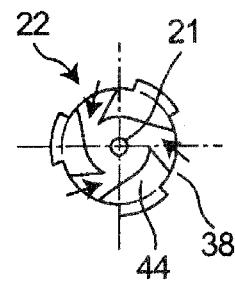
Figure 3:
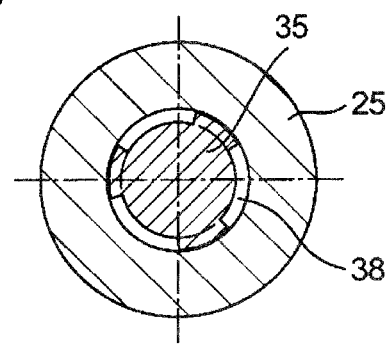
Figure 3:
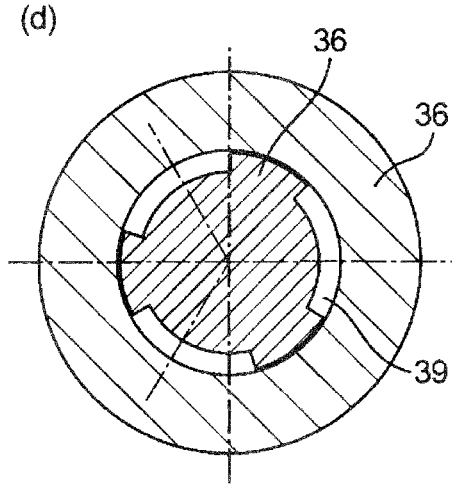
Figure 4:
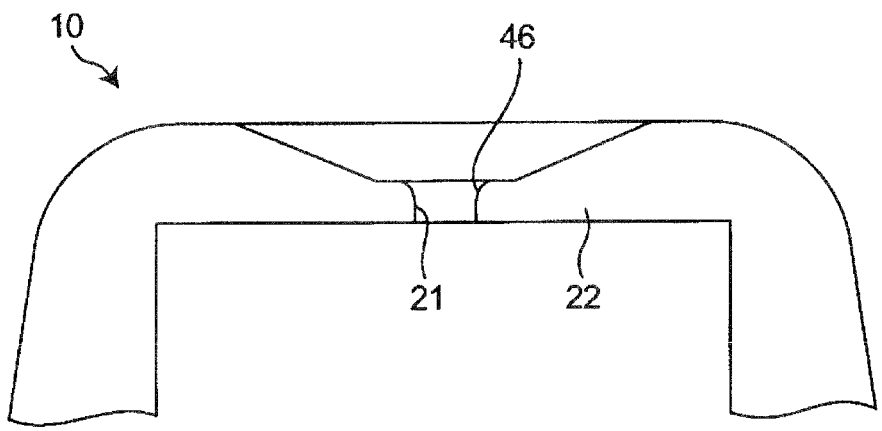
FIGS. 4(a) and 4(b) are enlarged cross-sectional views of the tip portion of the nozzle body, in which the tip portion is provided with the curved portion in FIG. 4(a) but not in FIG. 4(b).
Figure 4:
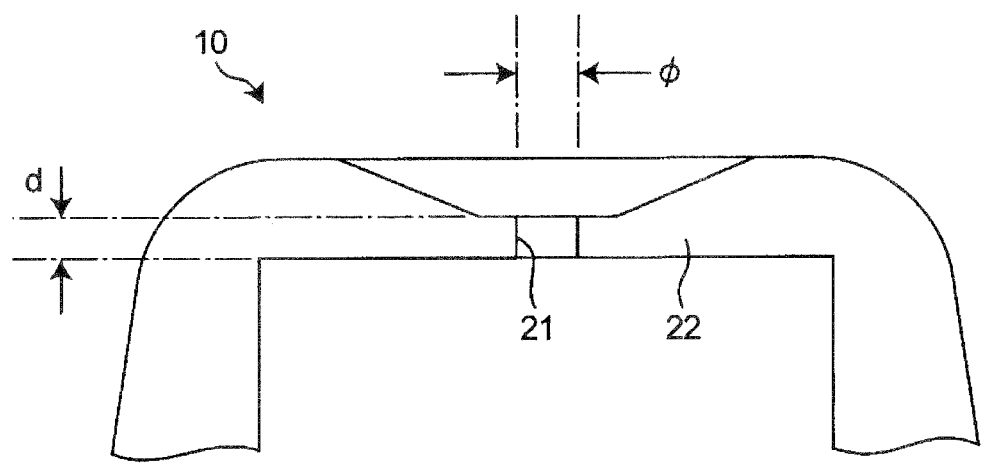

FIG. 3(a) is a vertical cross-sectional view of rhinal spray nozzle 10 of FIG. 2(b). FIGS. 3(b), 3(c) and 3(d) are horizontal cross-sectional views of rhinal spray nozzle 10 taken along B-B line, C-C line and D-D line of FIG. 3(a), respectively. Hollow nozzle body 20 defines internal space 24 of a substantially cylindrical shape. As shown in FIGS. 3(c) and 3(d), internal space 24 includes nozzle small-diameter portion 25 closer to nozzle orifice. 21 of hollow nozzle body 20, nozzle large-diameter portion 26 opposing to tip opening 6 of syringe body 4, and nozzle shoulder 27 which is designed to have a diameter continuously or step-wisely reducing from nozzle large-diameter portion 26 towards nozzle small-diameter portion 25.

On the other hand, solid packing rod 30 to be inserted within nozzle body 20 has outer wall 33 having a configuration substantially complementary with inner wall 23 of nozzle body 20 (internal space 24). As shown in FIGS. 2(a), 3(c) and 3(d), rod small-diameter portion 35 and rod large-diameter portion 36 include rod shoulder 37 which is designed to have a diameter continuously or step-wisely reducing from rod large-diameter portion 36 towards rod small-diameter portion 35.

Preferably, as illustrated in FIG. 3(a), inner wall 23 of nozzle body 20 is provided with protrusion 23a, while outer wall 33 of packing rod 30 is provided with recess 33a for receiving protrusion 23a. When packing rod 30 is fully inserted within internal space 24 of nozzle body 20, protrusion 23a may be closely fit in recess 33a to ensure connection between packing rod 30 and nozzle body 20.

Also as illustrated in FIGS. 2(a)-2(b) and 3(a)-3(d), packing rod 30 includes a plurality of grooves 38 and 39 circumferentially spaced from one another both on rod small-diameter portion 35 and rod large-diameter portion 36. Also, packing rod 30 is inserted within nozzle body 20 so as to define gap 40 between nozzle shoulder 27 and rod shoulder 37 (FIG. 3(a)). Thus, rhinal spray nozzle 10 assembled as illustrated in FIG. 2(b) has nozzle chamber 42 defined by grooves 38, 39 and gap 40, which allows fluid communication of formulation 2 delivered from tip opening 6 of syringe body 4 through nozzle chamber 42 to tip portion 22 of rhinal spray nozzle 10.

Furthermore, as shown in FIG. 3(b), packing rod 30 includes vortex-flow generation member 44 opposed to tip portion 22 of rhinal spray nozzle 10. Vortex-flow generation member 44 is configured to generate a vortex flow of formulation 2 that is delivered from each of grooves 38 of rod small-diameter portion 35 before being injected from nozzle orifice 21 of nozzle body 20. More particularly, the end portions of rod small-diameter portion 35 which define vortex-flow generation member 44 are formed so as to extend offset the vertical central axis of nozzle orifice 21. Thanks to generation of the vortex flow of formulation 2 before being injected from nozzle orifice 21, the spray angle of formulation 2 can be expanded to spray it in a more uniform manner.

As illustrated in FIGS. 3(c)-3(d), it is preferable to design grooves 38 of rod small-diameter portion 35 to be less than grooves 39 of rod large-diameter portion 36 so as to increase the pressure of formulation 2 in vortex-flow generation member 44 before being injected from nozzle orifice 21. Also, thanks to the diameters of rod large-diameter portion 36 and rod small-diameter portion 35 which are designed to continuously or step-wisely be reduced from the former to the latter, it is easier to insert rhinal spray nozzle 10 deeply into the nasal cavity and to spray the formulation towards the inferior nasal concha and even deeper portions of the patient. Thus preferably, the diameter of rod small-diameter portion 35 is smaller enough than the nasal cavity opening of the patient without minimizing fear of the patient.

EXAMPLES

According to the methods shown below, a gel base material and three kinds of virus stock solutions were prepared, and the gel base material and each virus stock solution were mixed as shown below to prepare influenza vaccine compositions as examples. Each viscosity was measured at 20° C. with a viscometer type E.

<Preparation of Gel Base Material>
Example of Gel Base Material (1)

| Ingredients | Amount | Process of Preparation |
| --- | --- | --- |
| Carboxy vinyl polymer | 11.0 mg | Each ingredient shown in the left column was mixed in the ratio corresponding to each weight shown there, and stirred to become homogeneous. Then, the mixture was given an outside shearing force by a high-speed rotation with an intermittently-jet-stream-generating-type high-speed spinning-type emulsifying device. The resulting base material whose viscosity was suitably adjusted with an outside shearing force was heated at 90° C. for 20 minutes to give a gel base material. Aspect: a clear and colorless gel base material, almost odorless. pH: 7.15 Viscosity: 4,000 mPa · s |
| L-arginine | 24.0 mg | |
| Concentrated glycerin | 20.0 mg | |
| Purified water | q. s. | |
| Total | 1.0 mL | |

<Preparation of Virus Stock Solution Comprising Inactivated Whole Influenza Virion>

Example of Virus Stock Solution (1)

| Ingredients | Amount | Process of Preparation |
| --- | --- | --- |
| Inactivated whole antigen of influenza virus A/Victoria/210/2009 (H3N2) | 180 µg HA | The strain for preparing the vaccine was seeded in the allantoic cavity of embryonated eggs and cultivated, and thent he virus suspension was collected. In order to clarify the virus suspension, it was centrifuged or filtered, and ultrafiltered to be concentrated. Then, in order to purify the virus, the filtrate was ultracentrifuged by, for example, sucrose density gradient centrifugation to give a purified virus solution. The purified virus solution was inactivated with formalin to give a purified inactivated virus solution. And then, the solution was ultrafiltered to give a virus stock solution. |
| Sodium hydrogen phosphate hydrate | 3.53 mg | |
| Sodium dihydrogen phosphate | 0.54 mg | |
| Sodium chloride | 8.50 mg | |
| Purified water | Total 1.0 mL | |

Example of Virus Stock Solution (2)

| Ingredients | Amount | Process of Preparation |
| --- | --- | --- |
| Inactivated whole antigen of influenza virus A/Indonesia/5/05 (H5N1) | 180 µg HA | The strain for preparing the vaccine was seeded in the allantoic cavity of embryonated eggs and cultivated, and then the virus suspension was collected. In order to clarify the virus suspension, it was centrifuged or filtered, and ultrafiltered to be concentrated. Then, in order to purify the virus, the filtrate was ultracentrifuged by, for example, sucrose density gradient centrifugation to give a purified virus solution. The purified virus solution was inactivated with formalin to give a purified inactivated virus solution. And then, the solution was ultrafiltered to give a virus stock solution. |
| Sodium hydrogen phosphate hydrate | 3.53 mg | |
| Sodium dihydrogen phosphate | 0.54 mg | |
| Sodium chloride | 8.50 mg | |
| Purified water | Total 1.0 mL | |

Example of Virus Stock Solution (3)

| Ingredients | Amount | Process of Preparation |
| --- | --- | --- |
| Inactivated whole antigen of influenza virus A/Calfornia/7/2009 (H1N1) pdm09 | 60 µg HA | The strain for preparing the vaccine was seeded in the allantoic cavity of embryonated eggs and cultivated, and then the virus suspension is collected. In order to clarify the virus suspension, it was centrifuged or filtered, and ultrafiltered to be concentrated. Then, in order |
| Inactivated whole antigen of influenza virus A/Victoria/365/2011 (H3N2) | 60 µg HA | |

-continued

| Ingredients | Amount | Process of Preparation |
|---|---|---|
| Inactivated whole antigen of influenza virus B/Wisconsin/01/2010 | 60 μg HA | to purify the virus, the filtrate was ultracentrifuged by, for example, sucrose density gradient centrifugation to give a purified virus solution. The purified virus solution was inactivated with β-propiolactone and formalin to give a purified inactivated virus solution. And then, the solution was ultrafiltered to give a virus stock solution. |
| Sodium hydrogen phosphate hydrate | 3.53 mg | |
| Sodium dihydrogen phosphate | 0.54 mg | |
| Sodium chloride | 8.50 mg | |
| Purified water | Total 1.0 mL | |

<Mixture of Gel Base Material and Virus Stock Solution>

Example of gel base material (1) and each of Examples of virus stock solution (1)-(3) mentioned above were mixed in the ratio of 1:1 under stirring to give each homogeneous influenza vaccine composition, Examples 1, 2, and 3, respectively. The compositions of each Example and their physical properties/spray-performances obtained with a spray device or a syringe-based squirt are shown below. The mixing under stirring can be completed softly and in a short time without stressing the inactivated whole antigen of virus. The quantities of each ingredient in the resulting influenza vaccine compositions, the physical properties thereof, and the spray-performances thereof derived by spraying the compositions with a suitable device are also shown below.

Example 1

| Ingredients | Amount | Physical property/ spray-performance |
|---|---|---|
| Inactivated whole antigen of influenza virus A/Victoria/210/2009 (H3N2) | 90 μg HA | pH: 7.25 Viscosity: 500 mPa · s Spray-performance in spraying 250 μL of the solution with a spray device: Mean particle size of sprayed formulation: 52 μm Ratio of particle size between 10 μm and 100 μm: 91.5% Spray angle from the device: 53° Spray density: full-corn uniformly-circle |
| Carboxy vinyl polymer | 5.50 mg | |
| L-arginine | 12.00 mg | |
| Concentrated glycerin | 10.00 mg | |
| Sodium hydrogen phosphate hydrate | 1.765 mg | |
| Sodium dihydrogen phosphate | 0.270 mg | |
| Sodium chloride | 4.25 mg | |
| Purified water | q.s. | |
| Total | 1.0 mL | |

Example 2

| Ingredients | Amount | Physical property/ spray-performance |
|---|---|---|
| Inactivated whole antigen of influenza virus A/Indonesia/5/05 (H5N1) | 90 μg HA | pH: 7.10 Viscosity: 430 mPa · s Osmotic pressure: 293 mOsm Spray-performance in spraying 250 μL of the |
| Carboxy vinyl polymer | 5.50 mg | |
| L-arginine | 12.00 mg | |
| Concentrated glycerin | 10.00 mg | solution with a spray device: Mean particle size of sprayed formulation: 55.2 μm Ratio of particle size between 10 μm and 100 μm: 95.0% Spray angle from the device: 51° Spray density: full-corn uniformly-circle |
| Sodium hydrogen phosphate hydrate | 1.765 mg | |
| Sodium dihydrogen phosphate | 0.270 mg | |
| Sodium chloride | 4.25 mg | |
| Purified water | q.s. | |
| Total | 1.0 mL | |

Example 3

| Ingredients | Amount | Physical property/ spray-performance |
|---|---|---|
| Inactivated whole antigen of influenza virus A/California/7/2009 (H1N1) pdm09 | 30 μg HA | pH: 7.15 Viscosity: 520 mPa · s Osmotic pressure: 295 mOsm Spray-performance in spraying 250 μL of the solution with a spray device: Mean particle size of sprayed formulation: 57.4 μm Ratio of particle size between 10 μm and 100 μm: 95.0% Spray angle from the device: 52° Spray density: full-corn uniformly-circle Spray-performance in spraying 250 μL of the solution with a syringe-based squirt Mean particle size of sprayed formulation: 56.5 μm Ratio of particle size between 10 μm and 100 μm: 88.2% Spray angle from the device: 51.48° Spray density: full-corn uniformly-circle |
| Inactivated whole antigen of influenza virus A/Victoria/365/2011 (H3N2) | 30 μg HA | |
| Inactivated whole antigen of influenza virus B/Wisconsin/01/2010 | 30 μg HA | |
| Carboxy vinyl polymer | 5.50 mg | |
| L-arginine | 12.00 mg | |
| Concentrated glycerin | 10.00 mg | |
| Sodium hydrogen phosphate hydrate | 1.765 mg | |
| Sodium dihydrogen phosphate | 0.270 mg | |
| Sodium chloride | 4.25 mg | |
| Purified water | q.s. | |
| Total | 1.0 mL | |

Example 4

| Ingredients | Amount | Physical property/ spray-performance |
|---|---|---|
| Inactivated whole antigen of influenza virus A/California/7/2009 (H1N1) pdm09 | 30 μg HA | pH: 7.17 Viscosity: 525 mPa · s Osmotic pressure: 291 mOsm Spray-performance in spraying 250 μL of the solution with a syringe-based |
| Inactivated whole antigen of influenza virus A/Victoria/365/2011 (H3N2) | 30 μg HA | |

-continued

Figure 5:
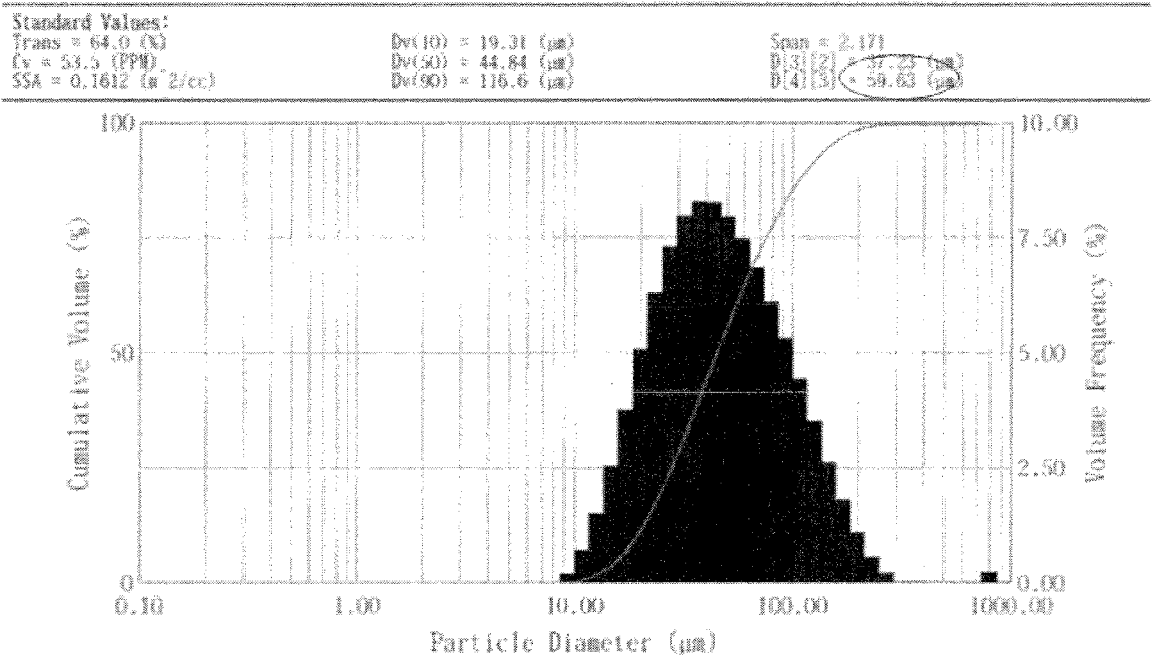
FIG. 5 shows a result that the particle size distribution of the formulation in Example 4 was measured with a laser diffraction particle size analyzer, which was sprayed with the syringe-based squirt of the present invention.
Figure 6:
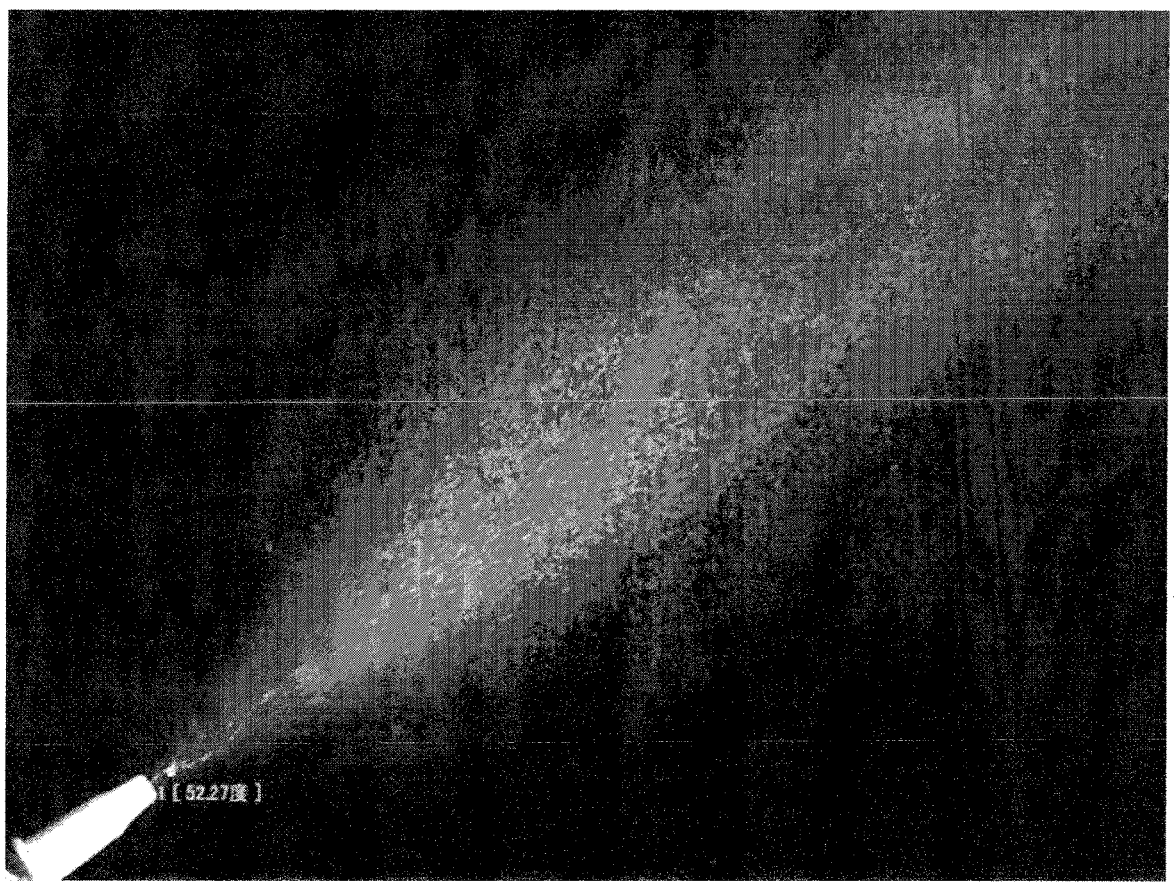
FIG. 6 shows a result that the spray angle of the formulation in Example 4 was measured with a high-speed microscope, which was sprayed from the tip of the nozzle in the syringe-based squirt of the present invention. The spray angle of the sprayed formulation was 52.27°.
Figure 7:
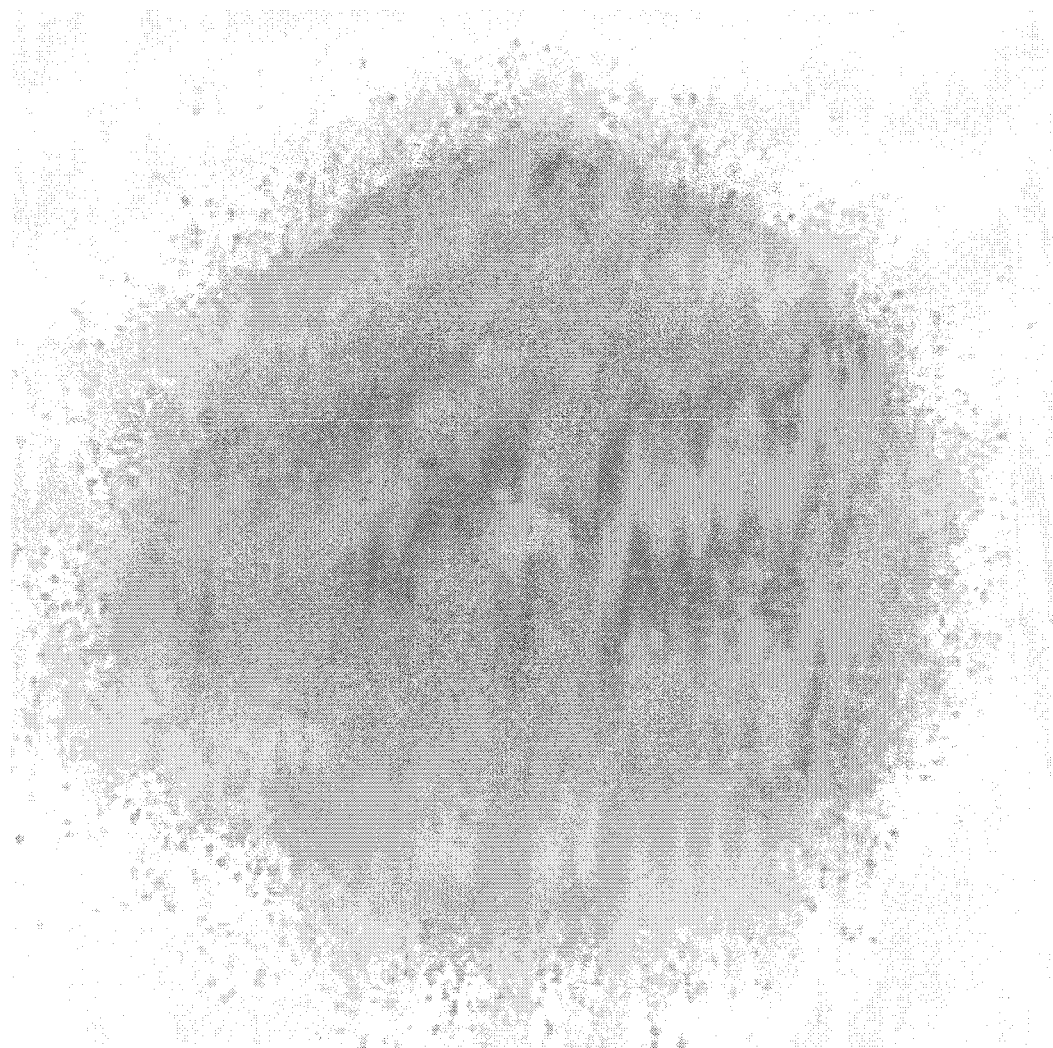
FIG. 7 shows a result that the spray behavior of the formulation in Example 4 was measured with a spray pattern test sheet, which was sprayed with the syringe-based squirt of the present invention. It was a uniform full-corn circle.

| Ingredients | Amount | Physical property/ spray-performance |
|---|---|---|
| Inactivated whole antigen of influenza virus B/Brisbane/60/2008 | 60 μg HA | squirt: Mean particle size of sprayed formulation: 59.6 μm (see, FIG. 5) |
| Carboxy vinyl polymer | 5.50 mg | |
| L-arginine | 12.00 mg | Ratio of particle size between 10 μm and 100 μm: 85.6% (see, FIG. 5) |
| Concentrated glycerin | 10.00 mg | |
| Sodium hydrogen phosphate hydrate | 1.765 mg | |
| Sodium dihydrogen phosphate | 0.270 mg | Spray angle from the device: 52.27° (see, FIG. 6) |
| Sodium chloride | 4.25 mg | |
| Purified water | q.s. | Spray density: full-corn uniformly-circle (see, FIG. 7) |
| Total | 1.0 mL | |

As an influenza vaccine composition without a gel base material, Comparative examples 1-4 were prepared according to the compositions shown in the following tables by optionally using the inactivated whole antigen used in the above examples.

Comparative Example 1

| Ingredients | Amount |
|---|---|
| Inactivated split antigen of influenza virus A/Uruguay/716/2007 (H3N2) | 90 μg HA |
| Sodium hydrogen phosphate hydrate | 3.53 mg |
| Sodium dihydrogen phosphate | 0.54 mg |
| Sodium chloride | 8.50 mg |
| Purified water | q.s. |
| Total | 1.0 mL |

Comparative Example 2

| Ingredients | Amount |
|---|---|
| Inactivated whole antigen of influenza virus A/Indonesia/5/05 (H5N1) | 90 μg HA |
| Sodium hydrogen phosphate hydrate | 3.53 mg |
| Sodium dihydrogen phosphate | 0.54 mg |
| Sodium chloride | 8.50 mg |
| Purified water | q.s. |
| Total | 1.0 mL |

Comparative Example 3

| Ingredients | Amount |
|---|---|
| Inactivated whole antigen of influenza virus A/California/7/2009 (H1N1) pdm09 | 30 μg HA |
| Inactivated whole antigen of influenza virus A/Victoria/365/2011 (H3N2) | 30 μg HA |
| Inactivated whole antigen of influenza virus B/Wisconsin/01/2010 | 30 μg HA |
| Sodium hydrogen phosphate hydrate | 3.53 mg |
| Sodium dihydrogen phosphate | 0.54 mg |
| Sodium chloride | 8.50 mg |
| Purified water | q.s. |
| Total | 1.0 mL |

Comparative Example 4

| Ingredients | Amount |
|---|---|
| Inactivated split antigen of influenza virus A/Calfornia/7/2009 (H1N1) pdm09 | 30 μg HA |
| Inactivated split antigen of influenza virus A/Victoria/365/2011 (H3N2) | 30 μg HA |
| Inactivated split antigen of influenza virus B/Wisconsin/01/2010 | 30 μg HA |
| Sodium hydrogen phosphate hydrate | 3.53 mg |
| Sodium dihydrogen phosphate | 0.54 mg |
| Sodium chloride | 8.50 mg |
| Purified water | q.s. |
| Total | 1.0 mL |

Test for Evaluating Immune Response (1)

With each influenza vaccine composition prepared in Example 1 and Comparative example 1, two groups composed of 4 adult volunteers in each group were vaccinated by nasal spray-administration with an appropriate disposable device, in an amount of 0.25 mL for one nostril (equivalent of 45 μg HA for both nostrils), twice at an interval of 3 weeks.

The blood and the washings of nasal cavity were consecutively collected, and the neutralizing antibody titer thereof for vaccine strain was measured and analyzed. The results are shown in Table 1 for Example 1, and Table 2 for Comparative example 1.

TABLE 1

| | | Neutralizing antibody titer in serum | | | Neutralizing antibody titer in washings of nasal cavity | | |
|---|---|---|---|---|---|---|---|
| No. | Sex | Initial (pre) | 3 weeks later | 6 weeks later | Initial (pre) | 3 weeks later | 6 weeks later |
| 01 | M | 80 | ≥1280 | ≥1280 | 40 | 640 | 640 |
| 02 | M | 5 | 5 | 40 | <20 | <20 | 40 |
| 03 | F | 20 | 160 | 320 | <20 | 40 | 40 |
| 04 | F | 640 | ≥1280 | ≥1280 | 40 | 40 | 160 |

TABLE 2

| | | Neutralizing antibody titer in serum | | | Neutralizing antibody titer in washings of nasal cavity | | |
|---|---|---|---|---|---|---|---|
| No. | Sex | Initial (pre) | 3 weeks later | 6 weeks later | Initial (pre) | 3 weeks later | 6 weeks later |
| 01 | M | 40 | 160 | 160 | 20 | 80 | 160 |
| 02 | M | <10 | <10 | 10 | 20 | 20 | 80 |
| 03 | M | 20 | 20 | 20 | 40 | 80 | 320 |
| 04 | M | <10 | <10 | <10 | 20 | 20 | 80 |

Comparing the results of the vaccine of Example 1 (the virus stock solution+the gel base material) and the vaccine of Comparative example 1 (a composition comprising the inactivated split antigen of influenza virus without the gel base material), the neutralizing antibody titer in serum of 3/4 subjects vaccinated with the vaccine of Comparative example 1 did not increase, while the neutralizing antibody titer in serum of 4/4 subjects vaccinated with the vaccine of Example 1 increased, and that significantly increased. The neutralizing antibody titer in washings of nasal cavity increased in all cases about both the vaccines of Example 1 and Comparative example 1, but the vaccine of Example 1 showed greater increase.

Test for Evaluating Immune Response (2)

With each influenza vaccine composition prepared in Example 2 and Comparative example 2, two groups composed of 25 adult volunteers for Example 2 and 24 adult volunteers for Comparative example 2 were vaccinated by nasal spray-administration with an appropriate disposable device, in an amount of 0.25 mL for one nostril (equivalent of 45 μg HA for both nostrils), twice at an interval of 3 weeks, and one more time about a half year later, totally three times.

The blood and the washings of nasal cavity were collected 3 weeks after the third vaccination, and the neutralizing antibody titer thereof to vaccine strain was measured and analyzed. The results are shown in Table 3.

TABLE 3

Variation of neutralizing antibody titer to A/Indonesia/5/05(H5N1)

| | Serum | | | | Washings of nasal cavity | | | |
|---|---|---|---|---|---|---|---|---|
| | Example 2 | | Comparative example 2 | | Example 2 | | Comparative example 2 | |
| | pre | post | pre | post | pre | post | pre | post |
| Geometric mean titer* (GMT) | 5.0 (<10) | 164.5 | 5.0 (<10) | 84.8 | 10.0 (<20) | 105.6 | 10.0 (<20) | 46.2 |
| GMT percentage of rise | | 32.9 | | 17.0 | | 10.5 | | 4.6 |

Comparing the results of the vaccine of Example 2 (the virus stock solution+the gel base material) and the vaccine of Comparative example 2 (only the virus stock solution), it was shown that the vaccine of Example 2 comprising the gel base material increased the immune response more greatly than that of Comparative example 2.

It is known that a human in a naive state who has never contacted influenza virus antigen (such as babies and children) induces less immune response. It is thought that the immune response in such susceptible individuals to influenza vaccine can be estimated by evaluating the immune response in healthy adults to the vaccine of highly pathogenic avian influenza virus (H5N1 stain) because almost all healthy adults have never contacted the avian influenza virus (i.e., in a naive state).

As shown in the above results, it has been found that even for susceptible individuals, the neutralizing antibody titer in serum and washings of nasal cavity can be induced in high level by nasally-vaccinating the vaccine of Example 2 (the virus stock solution+the gel base material) three times.

Analytical Test of Immune Response (3)

With each influenza vaccine composition prepared in Example 3, Comparative example 3 and Comparative example 4, two groups composed of 47 adult volunteers for Example 3 and 47 adult volunteers for Comparative example 3 were vaccinated by nasal administration with a syringe-based squirt, in an amount of 0.25 mL for one nostril (in total, μg HA/strain/0.5 mL for both nostrils), twice at an interval of 3 weeks. And, with the influenza vaccine composition prepared in Comparative example 4 (currently-used vaccine), a group composed of 38 adult volunteers was subcutaneously vaccinated once in an amount of 0.5 mL (15 μg HA/strain/0.5 mL).

The blood and the washings of nasal cavity were collected 3 weeks after the final vaccination (2nd or 1st), and the neutralizing antibody titer thereof to vaccine strain was measured and analyzed. Tables 4 and 5 show each result about the different kinds of influenza vaccine.

TABLE 4

| | Variation of neutralizing antibody titer to A/Calfornia/7/2009(H1N1)pdm09 Neutralizing antibody titer in serum | | | | | |
|---|---|---|---|---|---|---|
| | Example 3 nasal | | Comparative example 3 nasal | | Comparative example 4 subcutaneous | |
| | pre | post | pre | post | pre | post |
| Geometric mean titer* (GMT) | 64.12 | 160.00 | 80.00 | 119.13 | 110.00 | 285.98 |
| GMT percentage of rise | | 2.50 | | 1.49 | | 2.60 |

| | Variation of neutralizing antibody titer to A/Calfornia/7/2009(H1N1)pdm09 Neutralizing antibody titer in washings of nasal cavity | | | | | |
|---|---|---|---|---|---|---|
| | Example 3 nasal | | Comparative example 3 nasal | | Comparative example 4 subcutaneous | |
| | pre | post | pre | post | pre | post |
| Geometric mean titer* (GMT) | 20.90 | 56.99 | 21.85 | 46.36 | 25.35 | 25.82 |
| GMT percentage of rise | | 2.73 | | 2.12 | | 1.02 |

TABLE 5

| | Variation of neutralizing antibody titer to A/Victoria/365/2011(H3N2) Neutralizing antibody titer in serum | | | | | |
|---|---|---|---|---|---|---|
| | Example 3 nasal | | Comparative example 3 nasal | | Comparative example 4 subcutaneous | |
| | pre | post | pre | post | pre | post |
| Geometric mean titer* (GMT) | 88.7 | 245.39 | 86.12 | 169.72 | 148.45 | 332.22 |
| GMT percentage of rise | | 2.77 | | 1.97 | | 2.24 |

TABLE 5-continued Variation of neutralizing antibody
titer to A/Victoria/365/2011(H3N2)
Neutralizing antibody titer in washings of nasal cavity

|  | Example 3 nasal | | Comparative example 3 nasal | | Comparative example 4 subcutaneous | |
|---|---|---|---|---|---|---|
|  | pre | post | pre | post | pre | post |
| Geometric mean titer* (GMT) | 24.95 | 80.00 | 28.49 | 77.67 | 28.80 | 29.88 |
| GMT percentage of rise |  | 3.21 |  | 2.73 |  | 1.04 |

Comparing the results of the nasally-administered vaccine of Example 3 (the virus stock solution+the gel base material), the nasally-administered vaccine of Comparative example 3 (only the virus stock solution), and the subcutaneously-administered vaccine of Comparative example 4 (currently-used vaccine for subcutaneous-administration), it was shown that the nasally-administered vaccine of Example 3 comprising the gel base material increased the immune response more greatly than that of the nasally-administered vaccine of Comparative example 3. In addition, from the results in the washings of nasal cavity, the nasally-administered vaccine group of Example 3 showed the elicitation of neutralizing antibody on the nasal mucosa, but the subcutaneously-administered vaccine (currently-used vaccine) group of Comparative example 4 did not show the elicitation.

Thus, by filling a medical syringe having a tip opening in fluid communication with a syringe barrel, which is equipped with a rhinal spray nozzle comprising a hollow nozzle body having a tip portion defining a nozzle orifice thereon, a solid packing rod arranged within the nozzle body, and a nozzle chamber defined between the packing rod and the nozzle body to allow a fluid communication between the tip opening and the nozzle orifice, wherein the nozzle orifice has a diameter in a range between 0.25 mm and 0.30 mm with the formulation for nasally-administering influenza vaccine of Example 4 which was prepared with a gel base material prepared by adding an outside shearing force, a rhinovaccination system of influenza vaccine having spray-performance which is to control that (1) as for the particle-size-distribution of the sprayed composition, the mean particle size is in a range of 30 µm to 80 µm [59.6 µm], and the particle distribution between 10 µm and 100 µm is 80% or more [85.6%], (2) the spray density is uniform to form a homogeneous full-corn shape, and (3) the spray angle is adjusted in a range of 30° to 70° [52.27°] was able to be prepared.

DENOTATION OF REFERENCE NUMERALS

1: medical syringe, 2: pharmaceutical formulation, 3: syringe barrel, 4: syringe body, 5: plunger rod, 5a: fixing member, 6: opening, 7: piston, 8: finger flange, 9: plunger end member, 10: rhinal spray nozzle, 20: nozzle body, 21: nozzle orifice, 22: tip portion, 23: inner wall, 23a: protrusion, 24: internal space, 25: nozzle small-diameter portion, 26: large-diameter portion, 27: nozzle shoulder, 30: packing rod, 33: outer wall, 33a: recess, 35: rod small-diameter portion, 36: rod large-diameter portion, 37: rod shoulder, 38, 39: groove, 40: gap, 42: nozzle chamber, 44: vortex-flow generation member, 46: curved portion, 50: protection rap.

The invention claimed is:

1. A rhinovaccination system of influenza vaccine, comprising a syringe-based squirt filled with an influenza vaccine composition which comprises (i) an inactivated whole influenza virion, and (ii) a gel base material comprising carboxy vinyl polymer which has been treated with an outside shearing force to add spray-performance, and which is characterized by not comprising an adjuvant,
   wherein the syringe-based squirt is a medical syringe having a tip opening in fluid communication with a syringe barrel and a plunger longitudinally movable within in the syringe barrel to expel the vaccine composition through the tip opening, the syringe-based squirt being equipped with a rhinal spray nozzle provided on a tip end of the syringe, configured to release the vaccine composition as a fine mist, and comprising
      a hollow nozzle body having a tip portion defining a nozzle orifice thereon,
      a solid packing rod arranged within the nozzle body, and
      a nozzle chamber defined between the packing rod and the nozzle body to allow a fluid communication between the tip opening and the nozzle orifice,
   wherein the nozzle orifice has a diameter in a range between 0.25 mm and 0.30 mm,
   a wall of the tip portion of the nozzle body defining the nozzle orifice has thickness along the longitudinal direction of the nozzle body that is in a range between 0.20 mm and 0.30 mm,
   the nozzle body includes an inner wall having at least a portion formed in a cylindrical shape and the packing rod includes an outer wall with at least a portion formed in a cylindrical shape having a plurality of circumferentially spaced grooves,
   the nozzle chamber is defined between the at least portion of the inner wall of the nozzle body and the at least portion of the outer wall of the packing rod, and
   the packing rod includes a vortex-flow generation member opposed to the tip portion of the nozzle body.

2. The rhinovaccination system of influenza vaccine according to claim 1, wherein the amount of (i) the inactivated whole influenza virion is 1-500 µg HA/mL per type of vaccine virus strain.

3. The rhinovaccination system of influenza vaccine according to claim 1, wherein the influenza vaccine composition comprises 0.1 w/v % to 1.0 w/v % carboxy vinyl polymer.

4. The rhinovaccination system of influenza vaccine according to claim 1, wherein the spray-performance is to control (1) the particle-size-distribution of the sprayed composition, (2) the uniformity of spray density, and/or (3) the spray angle.

5. The rhinovaccination system of influenza vaccine according to claim 1, wherein the influenza vaccine composition is prepared by treating a gel base material comprising 0.5 w/v % to 2.0 w/v % carboxy vinyl polymer by adding an outside shearing force to control (1) the particle-size-distribution of the sprayed composition, (2) the uniformity of spray density, and/or (3) the spray angle, as spray-performance, to give a gel base material, and then
   mixing the resulting gel base material with a virus stock solution comprising an inactivated whole influenza virion homogeneously without stress.

6. The rhinovaccination system of influenza vaccine according to claim 1, wherein the influenza vaccine composition is prepared with a gel base material comprising carboxy vinyl polymer that is treated by adding an outside shearing force to add spray-performance which is to control that (1) as for the particle-size-distribution of the sprayed composition, the mean particle size is in a range of 30 μm to 80 μm, and the particle distribution between 10 μm and 100 μm is 80% or more, (2) the spray density is uniform to form a homogeneous full-corn shape, and (3) the spray angle is adjusted in a range of 30° to 70°.

7. The rhinovaccination system of influenza vaccine according to claim 1, wherein the influenza vaccine composition is prepared with a gel base material comprising carboxy vinyl polymer that is treated by adding an outside shearing force to add spray-performance which is to control that (1) as for the particle-size-distribution of the sprayed composition, the mean particle size is in a range of 40 μm to 70 μm, and the particle distribution between 10 μm and 100 μm is 90% or more, (2) the spray density is uniform to form a homogeneous full-corn shape, and (3) the spray angle is adjusted in a range of 40° to 60°.

8. The rhinovaccination system of influenza vaccine according to claim 1, wherein the nozzle orifice includes no curved portion.

9. The rhinovaccination system of influenza vaccine according to claim 1, wherein the vortex-flow generation member is formed so that a flow direction of the formulation from the grooves of the packing rod is offset to a central axis, thereby to generate a vortex flow of the formulation.

10. The rhinovaccination system of influenza vaccine according to claim 1, wherein the at least portion of the inner wall of the nozzle body is formed to have a cross section perpendicular to the injection direction which is continuously or step-wisely reduced towards the injection direction.

* * * * *